US010323260B2

(12) United States Patent
Kraemer et al.

(10) Patent No.: US 10,323,260 B2
(45) Date of Patent: *Jun. 18, 2019

(54) REDUCING BATCH TIME IN FERMENTATION PROCESSES BY SUBJECTING CORN-BASED FERMENTATION MEDIUM TO A XYLANASE AND A PECTINASE DURING FERMENTATION

(71) Applicants: DIREVO Industrial Biotechnology GmbH, Cologne (DE); BASF Enyzmes, LLC, San Diego, CA (US)

(72) Inventors: Marco Kraemer, Cologne (DE); Vitaly Svetlichny, Cologne (DE)

(73) Assignees: DIREVO Industrial Biotechnology GmbH, Cologne (DE); BASF Enzymes, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/501,593

(22) PCT Filed: Aug. 5, 2015

(86) PCT No.: PCT/EP2015/068124
§ 371 (c)(1),
(2) Date: Feb. 3, 2017

(87) PCT Pub. No.: WO2016/020468
PCT Pub. Date: Feb. 11, 2016

(65) Prior Publication Data
US 2017/0233768 A1 Aug. 17, 2017

Related U.S. Application Data

(60) Provisional application No. 62/033,327, filed on Aug. 5, 2014.

(30) Foreign Application Priority Data

Aug. 5, 2014 (EP) ..................................... 14179851

(51) Int. Cl.
*C12P 7/06* (2006.01)
*C12P 7/14* (2006.01)

(52) U.S. Cl.
CPC ...... *C12P 7/14* (2013.01); *C12P 7/06* (2013.01); *C12Y 302/01001* (2013.01); *C12Y 302/01008* (2013.01); *C12Y 302/01015* (2013.01); *C12P 2201/00* (2013.01); *Y02E 50/17* (2013.01)

(58) Field of Classification Search
None
See application file for complete search history.

(56) References Cited

FOREIGN PATENT DOCUMENTS

| WO | 2002038786 A1 | 5/2002 |
| WO | 2012084225 A1 | 6/2012 |
| WO | WO2012084225 | * 6/2012 |
| WO | 2014127851 A1 | 8/2014 |

OTHER PUBLICATIONS

PCT/EP2015/068124 International Search Report dated Oct. 23, 2015.
Li et al. "Monosaccharides and Ethanol Production from Superfine Ground Sugarcane Bagasse Using Enzyme Cocktail." Bioresources, Mar. 21, 2014, 9(2)2529-2540, North Carolina State University, College of Natural Resources, US.
Li et al. "Synergism of Cellulase, Xylanse, and Pectinase on Hydrolyzing Sugarcane Bagasse Resulting from Different Pretreatment Technologies." Bioresource Technology, Mar. 1, 2014, 155:258-265, Elsevier BV, GB.
Srichuwong et al. "Simultaneous Saccharification and Fermentation (SSF) of Very High Gravity (VHG) Potato Mash for the Production of Ethanol." Biomass and Bioenergy, 2009, 33:890-898.
Pervez et al. "Saccharification and Liquefaction of Cassava Starch: An Alternative Source for the Production of Bioethanol Using Amylolytic Enzymes by Double Fermentation Process." BMC Biotechnology, May 29, 2014, 14(49) 1-10.
Bals et al. "Evaluation of Ammonia Fibre Expansion (AFEX) Pretreatment for Enzymatic Hydrolysis of Switchgrass Harvested in Different Seasons and Locations." Biotechnology for Biofuels, 2010, 3:1-11.
Zhang et al. "Application of Simultaneous Saccharification and Fermentation (SSF) from Viscosity Reducing of Raw Sweet Potato for Bioethanol Production at Laboratory, Pilot and Industrial Scales." Bioresource Technology, 2011, 102:4573-4579.
Collares et al. "Optimization of Enzymatic Hydrolysis of Cassava to Obtain Fermentable Sugars." Journal of Zhejiang University—Science B (Biomedicine and Biotechnology), 2012, 13(7)579-586.
Rattanachomsri et al. "Simultaneous Non-Thermal Saccharification of Cassava Pulp by Multi-Enzyme Activity and Ethanol Fermentation by Candida Tropicalis." Journal of Bioscience and Bioengineering, 2009, 107(5)488-493. Elsevier, Japan.
Kongkiattikajorn, Jirasak. "Ethanol Production from Dilute-Acid Pretreated Cassava Peel by Fed-Batch Simultaneous Saccharification and Fermentation." International Journal of the Computer, The Internet and Management, 2012, 20(2)22-27.
Poonsrisawat et al. "Viscosity Reduction of Cassava for Very High Gravity Ethanol Fermentation Using Cell Wall Degrading Enzymes from Aspergillus Aculeatus." Process Biochemistry, Aug. 1, 2014, 49:1950-1957. Elsevier.

(Continued)

*Primary Examiner* — Christian L Fronda
(74) *Attorney, Agent, or Firm* — Wagenknecht IP Law Group PC (57) ABSTRACT

The present technology relates to methods of reducing the batch time in a fermentation process, wherein the fermentation medium is subjected before, during and/or after the fermentation process to an enzyme composition comprising at least a xylanase and a pectinase.

2 Claims, 3 Drawing Sheets

(56) References Cited

OTHER PUBLICATIONS

Zhu et al. "A Comparison of the Production of Ethanol Between Simulatenous Sacchrification and Fermentation and Separate Hydrolysis and Fermentation Using Unpretreated Cassava Pulp and Enzyme Cocktail." Bioscience, Biotechnology and Biochemistry, 2012, 76(4)671-678.

Sovorawet and Kongkiattikajorn. "Bioproduction of Ethanol in SHF and SSF from Cassava Stalks." KKU Research Journal (Khan Kaen University, Thailand) 2012, 17(4)565-572.

* cited by examiner

FIGURE 3 ant) is referred to as "thin stillage". Dewatered wet cake is dried to provide "Distillers Dried Grains" (DDG) used as nutrient in animal feed. Thin stillage is typically evaporated to provide condensate and syrup (or "thick stillage") or may alternatively be recycled directly to the slurry tank as "backset". Condensate may either be forwarded to a methanator before being discharged or may be recycled to the slurry tank. The syrup consisting mainly of limit dextrins and non-fermentable sugars may be blended into DDG or added to the wet cake before drying to produce DDGS (Distillers Dried Grain with Solubles).

REDUCING BATCH TIME IN FERMENTATION PROCESSES BY SUBJECTING CORN-BASED FERMENTATION MEDIUM TO A XYLANASE AND A PECTINASE DURING FERMENTATION

CROSS REFERENCE TO RELATED APPLICATIONS

This is a US national phase application under 35 U.S.C. § 371 of international application no. PCT/EP2015/068124, filed 5 Aug. 2015, which claims benefit of priority to EP application no. 14179851.2, filed 5 Aug. 2014, and U.S. provisional application No. 62/033,327, filed 5 Aug. 2014; the entire content of each is herein incorporated by reference in its entirety.

FIELD OF THE INVENTION

The present disclosure relates to improved processes of producing fermentation products from starch-containing material using a fermenting organism.

BACKGROUND OF THE INVENTION

A vast number of commercial products that are difficult to produce synthetically are today produced by fermenting organisms. Such products include alcohols (e.g., butanol, ethanol, methanol, 1,3-propanediol); organic acids (e.g., acetic acid, citric acid, gluconate, gluconic acid, itaconic acid, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones. Fermentation is also commonly used in the consumable alcohol (e.g., beer and wine), dairy (e.g., in the production of yogurt and cheese), leather, and tobacco industries.

Fermentation products, such as ethanol, are produced by first degrading starch-containing material into fermentable sugars by liquefaction and saccharification and then converting the sugars directly or indirectly into the desired fermentation product using a fermenting organism. Liquid fermentation products such as ethanol are recovered from the fermented mash (often referred to as "beer" or "beer mash"), e.g., by distillation, which separate the desired fermentation product from other liquids and/or solids. The remaining faction, referred to as "whole stillage", is dewatered and separated into a solid and a liquid phase, e.g., by centrifugation. The solid phase is referred to as "wet cake" (or "wet grains" or "WDG") and the liquid phase (supernat- Ethanol plants have struggled to maintain profitability, which is highly variable depending upon corn price, demand and price of DDGS, tax credits, gasoline consumption, ethanol exports, and changes to the Renewable Fuels Standard (RFS) mandates. New technologies for energy savings, higher yield of ethanol and higher value for co-products as well as various oil separation technologies contribute to the profitability of producing ethanol.

Therefore, there is a need for providing processes that can increase the yield of the fermentation product and thereby reduce the production costs. It is an object of the present invention to provide improved processes for producing fermentation products.

BRIEF SUMMARY OF THE INVENTION

The present invention relates to processes of producing fermentation products from starch-containing material using a fermenting organism.

In one aspect, the present disclosure relates to methods of reducing the batch time in a fermentation process comprising the steps of:
  i) Converting starch containing material to fermentable sugars
  ii) Fermentation of the fermentable sugars with a microorganism to fermented mash
  iii) Subjecting the fermentation medium before, during and/or after the fermentation process to an enzyme composition comprising a xylanase and a pectinase,
  iv) Separation of the fermentation product in the fermented mash.

In another aspect, the present disclosure relates to methods of producing a fermentation product from starch containing material, said method comprising the steps of:
  i) Converting starch containing material to fermentable sugars
  ii) Fermentation of the fermentable sugars with a microorganism to fermented mash
  iii) Subjecting the fermentation medium before, during and/or after the fermentation process to an enzyme composition comprising a xylanase and a pectinase,
  iv) Separation of the fermentation product in the fermented mash In another aspect, the present disclosure pertains to methods of producing a fermentation product, comprising
  (a) liquefying a starch-containing material with an alpha-amylase; optionally pre-saccharifying the liquefied material before step (b);
  (b) saccharifying the liquefied material;
  (c) fermenting using a fermentation organism; wherein an enzyme composition comprising a xylanase and a pectinase are present or added during the optional presaccharification step, saccharification step (b), and/or fermentation step (c), or simultaneous saccharification and fermentation.

DESCRIPTION OF THE INVENTION

The object of the present disclosure is to provide methods/processes of producing fermentation products from starch-containing material using a fermenting organism.

In an advantageous embodiment, the present disclosure pertains to methods of reducing the batch time in a fermentation process comprising the steps of:
i) Converting starch containing material to fermentable sugars
ii) Fermentation of the fermentable sugars with a microorganism to fermented mash
iii) Subjecting the fermentation medium before, during and/or after the fermentation process to an enzyme composition comprising a xylanase and a pectinase,
iv) Separation of the fermentation product in the fermented mash.

By subjecting/adding the fermentation medium before, during and/or after the fermentation process to an enzyme composition according to the present disclosure, the following positive technical effects could be identified:
  Oil recovery increased from ~3400-3600 gallons per day to ~4200-4300, or 17-27%
  Oil gallons per bushel increased from ~0.78 to ~0.91 or 17% during the same trial period
  Fermentation time data showed a decrease of up to 6 hours
  Ethanol yield date indicated an uptick of at least 3%

In an advantageous embodiment, the present disclosure relates to methods of producing a fermentation product from starch containing material, said method comprising the steps of:
i) Converting starch containing material to fermentable sugars
ii) Fermentation of the fermentable sugars with a microorganism to fermented mash
iii) Subjecting the fermentation medium before, during and/or after the fermentation process to an enzyme composition comprising a xylanase and a pectinase,
iv) Separation of the fermentation product in the fermented mash Stillage or Whole stillage is the product which remains after the mash has been converted to sugar, fermented and distilled into ethanol. Stillage can be separated into two fractions, such as, by centrifugation or screening: (1) wet cake (solid phase) and (2) the thin stillage (supernatant). The solid fraction or distillers' wet grain (DWG) can be pressed to remove excess moisture and then dried to produce distillers' dried grains (DDG). After ethanol has been removed from the liquid fraction, the remaining liquid can be evaporated to concentrate the soluble material into condensed distillers' solubles (DS) or dried and ground to create distillers' dried solubles (DDS). DDS is often mixed with DDG to form distillers' dried grain with solubles (DDGS). DDG, DDGS, and DWG are collectively referred to as distillers' grain(s).

In one embodiment of the present disclosure enzymes were added during and/or after the fermentation in the production process to the fermented mash and/or the fermentation medium and before the separation step like distillation, where the desired fermentation main product is separated from the rest of the fermented mash. The enzymes according to the present disclosure were capable of degrading components in the fermented mash (beer or beer mash) and/or the fermentation medium.

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof. Recovery Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

The feedstock for producing the fermentation product may be any starch-containing material, preferably starch-containing plant material, including: tubers, roots, whole grain; and any combination thereof. The starch-containing material may be obtained from cereals. Suitable starch-containing material includes corn (maize), wheat, barley, cassava, sorghum, rye, potato, or any combination thereof. Corn is the preferred feedstock, especially when the fermentation product is ethanol. The starch-containing material may also consist of or comprise, e.g., a side stream from starch processing, e.g., C6 carbohydrate containing process streams that may not be suited for production of syrups. Whole stillage typically contains about 10-15 wt-% dry solids. Whole stillage components include fiber, hull, germ, oil and protein components from the starch-containing feedstock as well as non-fermented starch.

Production of a fermentation product is typically divided into the following main process stages:
a) Reducing the particle size of starch-containing material, e.g., by dry or wet milling;
b) Cooking the starch-containing material in aqueous slurry to gelatinize the starch,
c) Liquefying the gelatinized starch-containing material in order to break down the starch (by hydrolysis) into maltodextrins (dextrins);
d) Saccharifying the maltodextrins (dextrins) to produce low molecular sugars (e.g., DP1-2) that can be metabolized by a fermenting organism;
e) Fermenting the saccharified material using a suitable fermenting organism directly or indirectly converting low molecular sugars into the desired fermentation product;
f) Recovering the fermentation product, e.g., by distillation in order to separate the fermentation product from the fermentation mash.

As also explained in the "Background"-section above whole stillage is a by-product consisting of liquids and solids remaining after recovery (e.g. by distillation) of a desired fermentation product from fermented mash (beer mash). According to the invention the fermentation product may be any fermentation product, including alcohols (e.g., ethanol, methanol, butanol, 1,3-propanediol); organic acids (e.g., citric acid, acetic acid, itaconic acid, lactic acid, gluconic acid, gluconate, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones. Fermentation is also commonly used in the consumable alcohol (e.g., beer and wine), dairy (e.g., in the production of yogurt and cheese), leather, and tobacco industries. In a preferred embodiment the fermentation product is a liquid, preferably an alcohol, especially ethanol.

As mentioned above, the starch-containing material may be obtained from cereals. Suitable starch-containing material includes corn (maize), wheat, barley, cassava, sorghum, rye, triticale, potato, or any combination thereof.

Corn is the preferred feedstock, especially when the fermentation product is ethanol. The starch-containing material may also consist of or comprise, e.g., a side stream from starch processing, e.g., C6 carbohydrate containing process streams that may not be suited for production of syrups. Beer components include fiber, hull, germ, oil and protein components from the starch-containing feedstock as well as non-fermented starch, yeasts, yeast cell walls and residuals. Production of a fermentation product is typically divided into the following main process stages: a) Reducing the particle size of starch-containing material, e.g., by dry or wet milling; b) Cooking the starch-containing material in aqueous slurry to gelatinize the starch, c) Liquefying the gelatinized starch-containing material in order to break down the starch (by hydrolysis) into maltodextrins (dextrins); d) Saccharifying the maltodextrins (dextrins) to produce low molecular sugars (e.g., DP1-2) that can be metabolized by a fermenting organism; e) Fermenting the saccharified material using a suitable fermenting organism directly or indirectly converting low molecular sugars into the desired fermentation product; f) Recovering the fermentation product, e.g., by distillation in order to separate the fermentation product from the fermentation mash.

As mentioned above beer (or fermented mash) is the fermentation product consisting of ethanol, other liquids and solids of a desired fermentation product. According to the invention the fermentation product may be any fermentation product, including alcohols (e.g., ethanol, methanol, butanol, 1,3-propanediol); organic acids (e.g., citric acid, acetic acid, itaconic acid, lactic acid, gluconic acid, gluconate, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones. Fermentation is also commonly used in the production of consumable alcohol (e.g., spirits, beer and wine), dairy (e.g., in the production of yogurt and cheese), leather, and tobacco industries. In a preferred embodiment the fermentation product is a liquid, preferably an alcohol, especially ethanol. The beer contemplated according to the invention may be the product resulting from a fermentation product production process including above mentioned steps a) to f). However, the beer may also be the product resulting from other fermentation product production processes based on starch- and/or lignocellulose containing starting material.

The fermenting organism may be a fungal organism, such as yeast, or bacteria. Suitable bacteria may e.g. be *Zymomonas* species, such as *Zymomonas mobilis* and *E. coli*. Examples of filamentous fungi include strains of *Penicillium* species. Preferred organisms for ethanol production are yeasts, such as e.g. *Pichia* or *Saccharomyces*. Preferred yeasts according to the disclosure are *Saccharomyces* species, in particular *Saccharomyces cerevisiae* or baker's yeast.

Further, by adding the enzymes according to the present disclosure to the fermented mash or the fermentation medium before the distillation step is an advantage since the enzymes in the enzyme compositions are inactivated during the distillation.

Processes for producing fermentation products, such as ethanol, from a starch or lignocellulose containing material are well known in the art. The preparation of the starch-containing material such as corn for utilization in such fermentation processes typically begins with grinding the corn in a dry-grind or wet-milling process. Wet-milling processes involve fractionating the corn into different components where only the starch fraction enters into the fermentation process. Dry-grind processes involve grinding the corn kernels into meal and mixing the meal with water and enzymes. Generally two different kinds of dry-grind processes are used. The most commonly used process, often referred to as a "conventional process," includes grinding the starch-containing material and then liquefying gelatinized starch at a high temperature using typically a bacterial alpha-amylase, followed by simultaneous saccharification and fermentation (SSF) carried out in the presence of a glucoamylase and a fermentation organism. Another well-known process, often referred to as a "raw starch hydrolysis" process (RSH process), includes grinding the starch-containing material and then simultaneously saccharifying and fermenting granular starch below the initial gelatinization temperature typically in the presence of an acid fungal alpha-amylase and a glucoamylase.

In a process for producing ethanol from corn, following SSF or the RSH process the ethanol is distilled from the whole mash after fermentation. The resulting ethanol-free slurry, usually referred to as whole stillage, is separated into solid and liquid fractions (i.e., wet cake and thin stillage containing about 35 and 7% solids, respectively). The thin stillage is often condensed by evaporation into a thick stillage or syrup and recombined with the wet cake and further dried into distillers' dried grains with solubles distillers' dried grain with solubles (DDGS) for use in animal feed.

In an embodiment of the present disclosure the xylanase may preferably be of microbial origin, such as of fungal origin (e.g., *Aspergillus, Fusarium, Humicola, Meripilus, Trichoderma*) or from a bacterium (e.g., *Bacillus*). In a preferred embodiment the xylanase is derived from a filamentous fungus, preferably derived from a strain of *Aspergillus*, such as *Aspergillus aculeatus*; or a strain of *Humicola*, preferably *Humicola lanuginosa*. Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210). The xylanase may preferably be an endo-1,4-beta-xylanase, more preferably an endo-1,4-beta-xylanase of GH 10 or GH 11. Examples of commercial xylanases include SHEARZYME™, BIOFEED WHEAT™, HTec and HTec2 from Novozymes A/S, Denmark.

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8X212), and *Neurospora crassa* (SwissProt accession number Q7SOW4).

Examples of suitable bacterial xylanases include include xylanases derived from a strain of *Bacillus*, such as *Bacillus subtilis*, such as the one disclosed in U.S. Pat. No. 5,306,633 or Contemplated commercially available xylanases include SHEARZYM E™, BIOFEED WHEAT™, (from Novozymes AJS), Econase CE™ (from AB Enzymes), Depol 676™ (from Biocatalysts Ltd.) and SPEZYME™ CP (from Genencor Int.).).

Xylanase may be added in an amount effective in the range from $0.16\times10^6$-$460\times10^6$ Units per ton beer mash or fermentation medium.

Example for the Determination of Xylanase Activity (FXU)

The endoxylanase activity is determined by an assay, in which the xylanase sample is incubated with a remazol-xylan substrate (4-O-methyl-D-glucurono-D-xylan dyed with Remazol Brilliant Blue R, Fluka), pH 6.0. The incubation is performed at 50° C. for 30 min. The background of non-degraded dyed substrate is precipitated by ethanol. The remaining blue colour in the supernatant is determined spectrophotometrically at 585 nm and is proportional to the endoxylanase activity.

The endoxylanase activity of the sample is determined relatively to an enzyme standard.

The pectinase used in the methods according to the present disclosure may be any pectinase, in particular of microbial origin, in particular of bacterial origin, such as a pectinase derived from a species within the genera *Bacillus, Clostridium, Pseudomonas, Xanthomonas* and *Erwinia*, or of fungal origin, such as a pectinase derived from a species within the genera *Trichoderma* or *Aspergillus*, in particular from a strain within the species *A. niger* and *A. aculeatus*. Contemplated commercially available pectinases include Pectinex Ultra-SPL™ (from Novozymes), Pectinex Ultra Color (from Novozymes), Rohapect Classic (from AB Enzymes), Rohapect 10 L (from AB Enzymes). Pectinase may be added in an amount effective in the range from $1.4\times10^9$-$23500\times10^9$ Units per ton beer mash or fermentation medium.

Example for the Determination of Pectintranseliminase Unit (PECTU).

Proteases as used in the present disclosure are enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH 7

Suitable acid fungal proteases include fungal proteases derived from *Aspergillus, Mucor, Rhizopus, Candida, Coriolus, Endothia, Enthomophtra, Irpex, Penicillium, Sclerotium* and *Torulopsis*. Commercial proteases include GC 106™ and SPEZYME™ FAN (available from Genencor, USA). Suitable bacterial proteases, although not acidic proteases, include the commercially available products ALCALASE™ and NEUTRASE™ (available from Novozymes A/S).

A cellulase, used in accordance with the disclosure, may be any cellulase, in particular of microbial origin, in particular fungal or bacterial origin such as a cellulase derivable from a strain of a filamentous fungus (e.g., *Aspergillus, Trichoderma, Humicola, Fusarium*). Preferably, the cellulase acts on both cellulosic and lignocellulosic material. Preferred cellulases for use in the present invention include endo-acting cellulases, exo-acting celluases and cellobiases, and combinations thereof. Examples of commercially available cellulases suitable according to the present invention include, for example, CELLULCLAST™ (available from Novozymes A/S), LAMINEX™ and SPEZYME™ CP (Genencor Int.) and Econase CE™ (from AB Enzymes GmbH), Rohalase BX™ (from Ab Enzymes GmbH), Cellulase 13P™ (from Biocatalysts Ltd.).

Cellulase may be added in amounts effective in the range or from $0.03\times10^6$-$16\times10^6$ Units per ton substrate (in fermenting mash)

The method is based on the enzyme's degradation of a pectin solution by a transeliminase reaction, the double bonds formed result in an increase in the absorption at 238 nm which is followed by a spectrophotometer.

Reaction Conditions
Temperature: 30° C.±0.5° C.
pH: 3.50±0.02
Substrate: 0.24% Pectin (Obipektin, Brown Ribbon Pure, Art. no. 1.1B00.A. Lot no. 0304)
Enzyme concentration: 1.9-2.3 PECTU/mL
Reaction time: 6 minutes
Measuring time: 5 minutes
Wavelength: 238 nm The activity is determined relative to a PECTU standard. The result is given in the same units as for the standard, which is designated: PECTU—Pectintranseliminase Unit.

The term "alpha-amylase" means an alpha-1,4-glucan-4-glucanohydrolase (E.C. 3.2.1.1) that catalyzes the hydrolysis of starch and other linear and branched 1,4-glucosidic oligo- and polysaccharides.

In an embodiment, the xylanase is added in an amount of 1-30, e.g., 5-30 7-25, 10-20, 10-17, or 12-15 micrograms/g dry solids.

In an embodiment, the pectinase is added in an amount of 0.01-1.0, e.g., 0.015-0.08, 0.015-0.06, 0.015-0.04, or 0.02-0.03 FXU/g dry solids.

The saccharification and fermentation steps may be carried out either sequentially or simultaneously. The xylanase and the pectinase may be added during saccharification and/or after fermentation when the process is carried out as a sequential saccharification and fermentation process and before or during fermentation when steps (b) and (c) are carried out simultaneously (SSF process).

As mentioned above, the fermenting organism is preferably yeast, e.g., a strain of *Saccharomyces cerevisiae* or *Saccharomyces diastaticus*. In an advantageous embodiment a yeast strain of *Saccharomyces diastaticus* is used (SIHA Amyloferm®, E. Begerow GmbH&Co, Langenlonsheim, Germany) since their exo-amylase activity can split liquid starch and also dextrin, maltose and melibiose.

In the liquefaction step the gelatinized starch (downstream mash) is broken down (hydrolyzed) into maltodextrins (dextrins). To achieve starch hydrolysis a suitable enzyme, preferably an alpha-amylase, is added. Liquefaction may be carried out as a three-step hot slurry process. The slurry is heated to between 60-95° C., preferably 80-85° C., and an alpha-amylase may be added to initiate liquefaction (thinning). Then the slurry may be jet-cooked at a temperature between 95-140° C., preferably 105-125° C., for about 1-15 minutes, preferably for about 3-10 minutes, especially around about 5 minutes. The slurry is cooled to 60-95° C. and more alpha-amylase may be added to complete the hydrolysis (secondary liquefaction). The liquefaction process is usually carried out at a pH of 4.0 to 6.5, in particular at a pH of 4.5 to 6.

The saccharification step and the fermentation step may be performed as separate process steps or as a simultaneous saccharification and fermentation (SSF) step. The saccharification is carried out in the presence of a saccharifying enzyme, e. g. a glucoamylase, a beta-amylase or maltogenic amylase. Optionally a phytase and/or a protease is added.

Saccharification may be carried out using conditions well known in the art with a saccharifying enzyme, e.g., beta-amylase, glucoamylase or maltogenic amylase, and optionally a debranching enzyme, such as an isoamylase or a pullulanase. For instance, a full saccharification process may last up to from about 24 to about 72 hours, however, it is common to do a pre-saccharification for typically 40-90 minutes at a temperature between 30-65° C., typically about 60° C., followed by complete saccharification during fermentation in a simultaneous saccharification and fermentation process (SSF process). Saccharification is typically carried out at a temperature from 20-75° C., preferably from 40-70° C., typically around 60° C., and at a pH between 4 and 5, normally at about pH 4.5.

The most widely used process to produce a fermentation product, especially ethanol, is the simultaneous saccharification and fermentation (SSF) process, in which there is no holding stage for the saccharification, meaning that a fermenting organism, such as a yeast, and enzyme(s), including the hemicellulase(s) and/or specific endoglucanase(s), may be added together. SSF is typically carried out at a temperature from 25° C. to 40° C., such as from 28° C. to 35° C., from 30° C. to 34° C., preferably around about 32° C. In an embodiment, fermentation is ongoing for 6 to 120 hours, in particular 24 to 96 hours.

During and/or after the fermentation, the fermented mash is subjected to an enzyme composition according to the present disclosure. In an embodiment, the enzyme composition comprises a xylanase and a pectinase.

In further embodiments, the enzyme composition comprises added in the methods according to the present disclosure comprises further a cellulose and/or a glucanase.

In an advantageous embodiment, the enzyme composition added in the methods according to the present disclosure comprises a xylanase, a pectinase, a cellulose and a glucanase.

In advantageous embodiment, the enzyme compositions comprise a beta-1,3-glucanase and/or a 1,6-beta-glucanase.

In an embodiment, the enzyme composition comprises a beta-1,3-glucanase and a 1,6-beta-glucanase. In another embodiment, the enzyme composition comprises a xylanase. In an advantageous embodiment, the enzyme composition comprises a beta-1,3-glucanase and a xylanase. In another embodiment, the enzyme composition comprises a beta-1,3-glucanase, a 1,6-beta-glucanase and a xylanase.

In further embodiments, the enzyme composition comprises in addition a pectinase and/or a protease. In an example the enzyme composition comprises a beta-1,3-glucanase, a xylanase and a protease. In another example the enzyme composition comprises a beta-1,3-glucanase, a xylanase and a pectinase.

In a further embodiment, enzyme composition comprises a mannanase. In an advantageous embodiment the enzyme composition comprises a mannanase and a beta-1,3-glucanase.

Beta-1,3-glucanases as used herein are enzymes capable of degrading of glucan. Glucan and chitin are far more resistant to microbial degradation than cellulose, which is the major constituent of the cell wall of many yeasts and fungi-like organisms. Glucan is predominantly beta-1,3-linked with some branching via 1,6-linkage (Manners et al., Biotechnol. Bioeng, 38, p. 977, 1973), and is known to be degradable by certain beta-1,3-glucanase systems. beta-1,3-glucanase includes the group of endo-beta-1,3-glucanases also called laminarinases (E.C. 3.2.1.39 and E.C. 3.2.1.6, Enzyme Nomenclature, Academic Press, Inc. 1992).

A number of beta-1,3-glucanase genes and uses thereof have been disclosed in the prior art. An example is DD 226012 (Akad. Wissenshaft, DDR) which concerns a method for production of a Bacillus beta-1,3-glucanase. Further, JP 61040792 A (DOI K) describes a cell wall-cytolase beta-1,3-glucanase recombinant plasmid for removing the cell walls of yeast. The gene is derived from Arthrobacter and is transformed in Escherichia group bacteria. EP 440.304 concerns plants provided with improved resistance against pathogenic fungi transformed with at least one gene encoding an intracellular chitinase, or in intra- or extracellular beta-1,3-glucanase. The matching recombinant polynucleotides is also disclosed. WO 87/01388 (The Trustees of Columbia University) describes a method for preparing cell lytic enzymes, such as beta-1,3-glucanases, which can be produced by Oerksovia. WO 92/03557 (Majesty (Her) in Right of Canada) discloses a recombinant DNA expression vector comprising a 2.7 kb DNA sequence, derived from Oerskovia xanthineolytica, encoding a beta-1,3-glucanase. From WO 92/16632 a recombinant DNA sequence coding for a novel protein with beta-1,3-glucanase activity, is known.

Examples for Commercial Available Beta-1,3-Glucanase are Rohalase BX from AB Enzymes and Rapidase Glucalees from DSM.

Hemicellulases as used herein are enzymes capable to break down hemicellulose. Any hemicellulase suitable for use in hydrolyzing hemicellulose, preferably into xylose, may be used. Preferred hemicellulases include acetylxylan esterases, endo-arabinases, exo-arabinases, arabinofuranosidases, feruloyl esterase, endo-galactanases, exo-galactanases, glucuronidases, mannases, xylanases, and mixtures of two or more thereof. Preferably, the hemicellulase for use in the present invention is an exondo-acting hemicellulase, and more preferably, the hemicellulase is an exo-acting hemicellulase which has the ability to hydrolyze hemicellulose under acidic conditions of below pH 7, preferably pH 3-7.

In one aspect, the hemicellulase(s) comprises a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

In a particular embodiment, the process of the present disclosure further comprises, prior to liquefying the starch-containing material the steps of:
reducing the particle size of the starch-containing material, preferably by milling; and
forming a slurry comprising the starch-containing material and water.

The aqueous slurry may contain from 10-55 w/w % dry solids (DS), preferably 25-45 w/w % dry solids (DS), more preferably 30-40 w/w % dry solids (DS) of the starch-containing material. The slurry is heated to above the gelatinization temperature and an alpha-amylase, preferably a bacterial and/or acid fungal alpha-amylase, may be added to initiate liquefaction (thinning). The slurry may be jet-cooked to further gelatinize the slurry before being subjected to an alpha-amylase in step (a).

In a preferred embodiment, the starch containing material is milled cereals, preferably barley or corn, and the methods comprise a step of milling the cereals before step (a). In other words, the disclosure also encompasses methods, wherein the starch containing material is obtainable by a process comprising milling of cereals, preferably dry milling, e. g. by hammer or roller mils. Grinding is also understood as milling, as is any process suitable for opening the individual grains and exposing the endosperm for further processing. Two processes of milling are normally used in alcohol production: wet and dry milling. The term "dry milling" denotes milling of the whole grain. In dry milling the whole kernel is milled and used in the remaining part of the process Mash formation. The mash may be provided by forming a slurry comprising the milled starch containing material and brewing water. The brewing water may be heated to a suitable temperature prior to being combined with the milled starch containing material in order to achieve a mash temperature of 45 to 70° C., preferably of 53 to 66° C., more preferably of 55 to 60° C. The mash is typically formed in a tank known as the slurry tank.

Subsequent to fermentation the fermentation product may be separated from the fermentation medium. The slurry may be distilled to extract the desired fermentation product or the desired fermentation product from the fermentation medium by micro or membrane filtration techniques. Alternatively the fermentation product may be recovered by stripping. Methods for recovering fermentation products are well known in the art. Typically, the fermentation product, e.g., ethanol, with a purity of up to, e.g., about 96 vol. % ethanol is obtained.

Thus, in one embodiment, the methods of the disclosure further comprise distillation to obtain the fermentation product, e.g., ethanol. The fermentation and the distillation may be carried out simultaneously and/or separately/sequentially; optionally followed by one or more process steps for further refinement of the fermentation product.

Further details on how to carry out liquefaction, saccharification, fermentation, distillation, and recovering of ethanol are well known to the skilled person.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation as mentioned above. Ethanol with a purity of up to about 96 vol. % can be obtained, which can be used as, for example, fuel ethanol, drinking ethanol, i.e., potable neutral spirits, or industrial ethanol.

The inventions described and claimed herein are not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

EXAMPLES

1. Reduction of Batch Time in a Bioethanol Plant

Bioethanol production cost is influenced by several factors. One is capacity usage, i.e. time of fermentation. If less time is needed for the same amount of product both capital cost and operational cost per batch will be reduced, capital cost via less depreciation and operational cost via reduced power usage for stirring.

This example describes how fermentation batch time can be reduced in industrial scale bioethanol fermentation by application of an enzyme composition comprising xylanases, cellulases, glucanases and pectinases.
Preparation of Inoculation:

In the present case of a bioethanol plant the preculture for bioethanol fermentation is prepared in two steps. The yeast is mixed with 350 gallons of water and heated to 37° C. After one hour of conditioning it is pumped into the inoculation tank and mixed with another 7500 gallons of mash (32% corn (w/v), ground with hammer mill number 5 screen, liquefied and saccharified material). Next the inoculum is inspected and released for application. The inoculum may stay in the inoculation tank for several days. To start fermentation the content of the inoculation tank is transferred to the fermenter. 3 out of 4 times the inoculation tank is not emptied completely but a remaining amount is kept to inoculate a next dose of mash.
Treatment of Fermentation Cultures:

In this case 25 fermenters were not treated with enzyme (0 g/t enzyme composition; "Control"), then 32 fermenters were treated with the enzyme composition comprising xylanases, cellulases, glucanases and pectinases from the beginning of the fermentation in different concentrations:

13 fermenters with 60 g/t enzyme composition (Conc1)
19 fermenters with 30 g/t enzyme composition (Conc2)
Fermentation Process:

The fermentation starts with filling of the fermenter by transferring the inoculum. In parallel the fermenter is filled with mash (32% corn (w/v), ground with hammer mill number 5 screen) to a total of 371,000 gallons. The fermenter is heated to 30° C. The filling procedure is completed after approximately 14.5 hours. Fermentation is completed after approximately 70 hours and the fermentation broth is then transferred to the beer well until further processing.
Sampling of Fermentation:

Samples are taken initially at fermentation start. Samples are taken every 6 hours within a defined 3 hour interval. Samples are analyzed via HPLC for ethanol, glucose, maltose, DP3, DP4+, lactic acid, acetic acid and glycerol. In addition temperature, pH and Brix are monitored. All data sets are single measurements.
Definition of Batch Time Start of fermentation is defined by the time when the inoculum is being transferred to the fermenter. Since the entire filling process of inoculums and mash takes up to 14.5 hours, data sets prior to 14.5 hours are being ignored in evaluation of ethanol production.

The fermentation broth is kept in the fermenter for a defined time regardless of completion of ethanol production. End of fermentation is defined by transfer of the fermented mash to the beer well. When exceeding about 13% (w/v) ethanol the ethanol production rate significantly decreases and plateau phase is reached. For evaluation of ethanol production data sets exceeding 13% (w/v) of ethanol are being ignored.

Hence, data sets referring to a sampling time greater than 14.5 hours and including but not exceeding the first recognition of ethanol concentration higher than 13% are used for evaluation of the batch time.
Evaluation For evaluation a logarithmic regression curve was fitted to the data points between 14.5 hours and the first data point exceeding 13% w/v ethanol (for example see FIG. 1). The achievement of 13% w/c ethanol was determined via calculation using the functional equation of the fitted curve.

Figure 1:
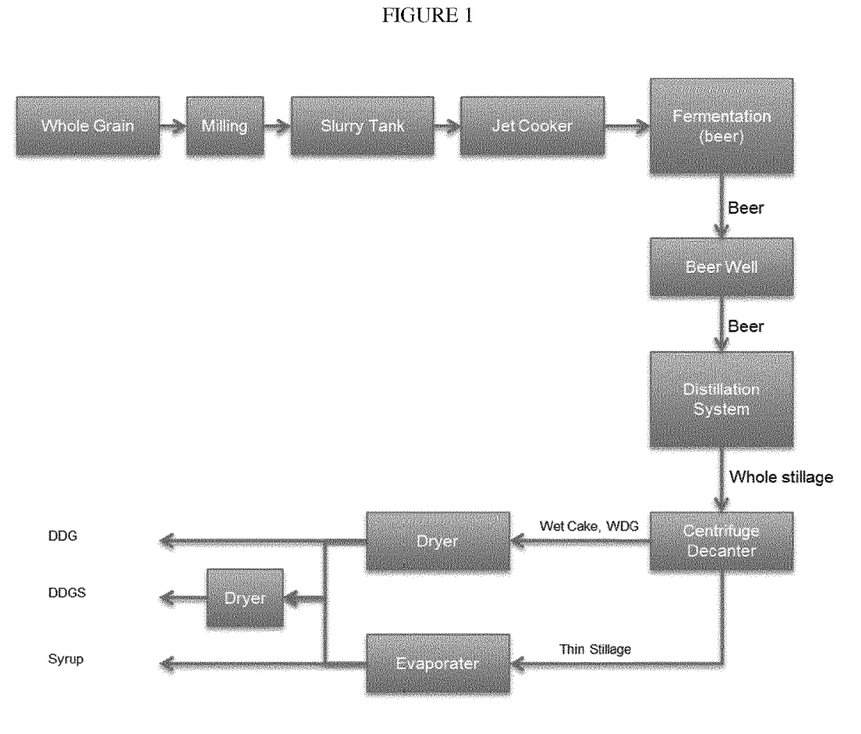
FIG. 1 schematically shows an ethanol production process.

FIG. 1 shows the effect of an enzyme composition comprising xylanases, cellulases, glucanases and pectinases on ethanol fermentation performance. Determination of the ethanol production is shown exemplarily for selected fermentation batches for Control, Conc1 and Conc2.

Results

Results of the evaluation of all 57 data sets are summarized in

Table 1. Unpaired t test rated the decreased fermentation time for both enzyme concentrations as extremely statistically significant. Therefore results confirm that the enzyme composition comprising xylanases, cellulases, glucanases and pectinases reduces batch time by an average of 5 h in the case of Conc2 and by an average of 5.5 h in the case of conc1, and accelerates ethanol production during the fermentation of mash by 11% to 12%.

TABLE 1

Evaluation of a total of 57 data sets for bioethanol production in industrial scale.

|  | Fermentation time to 13% ethanol (w/v) [h] | Standard deviation [h] | Number of batches |
| --- | --- | --- | --- |
| Control | 45.38 | 4.36 | 25 |
| Conc1 | 39.89 | 1.59 | 13 |
| Conc2 | 40.33 | 3.94 | 19 |

|  | Δ Fermentation time [h] | Δ Fermentation time [%] | Unpaired t test P value |
| --- | --- | --- | --- |
| Control − Conc1 | 5.48 | 12% | 0.0001 |
| Control − Conc2 | 5.05 | 11% | 0.0003 |

2. Accelerated Production of Ethanol

The effectiveness of any fermentative process is defined by the production rate of the target product. Therefore increasing the fermentative production rate of ethanol, i.e. the acceleration of ethanol production is highly economical.

For that example the ethanol production of the fermentation process in presence and absence of additional enzymes accelerating ethanol concentration were tested.

Three different setups were tested.

In the first fermentor (Fermentor#1) the fermentation cultivation was not treated with enzymes (0 g/t xylanase; 0 g/t pectinase), in the second and third fermentor (Fermentor#2 to #3) the fermentation cultivation was treated with the enzyme composition comprising a xylanase and a pectinase from the beginning of the fermentation in different concentrations (from 75 g/t to 200 g/t xylanase and from 75 g/t to 200 g/t pectinase).

The trials were performed in 2 L fermentation scale. Samples were taken during the fermentation process and the concentrations of ethanol were determined by HPLC.

EXAMPLES

In one embodiment, the process of the production of ethanol from corn was performed as follows:

A) Process for Producing Fermentation Products a) Reducing the particle size of the starch-containing material by milling
   corn (Company Pannonia, Hungary) was milled to <2 mm particle size (coffee mill, company Brunn)

b) Forming a slurry comprising the starch-containing material and water
   1.5 kg milled corn was added to 4.96 L ml warm tap water (water hardness 3.57 mmol/L) at 35° C. to obtain a 25% solid solution with a final volume of 6 L in a Biostat C fermentor (company Sartorius) leading to a pH of about 5.6.

c) Liquefying of the starch-containing material
   temperature was increased to 90° C.
   1 ml α-amylase "α-amylase VF-Kartoffel" (Schliessmann, Nr. 5049) was diluted in 10 ml tap water and then the diluted amylase was added to the slurry
   temperature was increased to 90° C.
   the fermentor was incubated for 90 min at 90° C. and 450 rpm
   the slurry was cooled to 30° C., pH was adjust to ~4 with 30% $H_2SO_4$ d) Saccharifying of the liquefied material obtained
   1.5 ml glucoamylase "Amylase GA 500" (Schliessmann, Nr. 5042) was diluted in 10 ml sterile tap water and then the diluted glucoamylase was added to the slurry, which is the saccharified liquefied material.

e) Fermentation
   1.8 g $(NH_4)2SO_4$ (i.e. 300 ppm ammonium sulphate) was added to the 6 L saccharified liquefied material.
   the saccharified liquefied material containing 300 ppm ammonium sulphate in the Biostat C fermentor was stirred with 800 rpm for 5 min to distribute everything evenly.
   the saccharified liquefied material containing 300 ppm ammonium sulphate (i.e. mash) was distributed in 1500 g single portions into four 2 L Biostat B fermentors (company Sartorius) containing a horseshoe mixer.
   Enzyme stock preparation: 2.5 g of the pectinase (Pec3) with 90349 U/mL and 2.5 g of the xylanase (Xyl16) with 10027 U/mL were added into a 50 mL graduated cylinder and filled to 50 mL with tap water.
   The enzyme stock was transferred into a 50 mL tube and then stored at 4° C. until use within one hour.
   The following volumes of the enzyme stock preparation were added to the 2 L Biostat B fermentor containing 1500 g of the saccharified liquefied material containing 300 ppm ammonium sulphate.
   Fermentor #1: 0 mL of the enzyme stock preparation leading to 0 g/t of pectinase and 0 g/t of xylanase
   Fermentor #2: 2.25 mL of the enzyme preparation leading to 75 g/t of pectinase and 75 g/t of xylanase
   Fermentor #3: 6.00 mL of the enzyme preparation leading to 200 g/t of pectinase and 200 g/t of xylanase
   Yeast propagation: 300 ml autoclaved YNB (yeast nitrogen base) medium plus glucose with 10 g/L glucose medium resulting in pH 5.7 in a 1 L cultivation flasks, which had been inoculated with 2 ml yeast (Ethanol RED, company Fermentis) from a −80° C. cryo stock containing 20% glycerol, were incubated for 23 hours (30° C., 150 rpm) leading to the yeast culture.
   Each of the three fermentors (Fermentor #1 to #3) was inoculated by 60 mL of the yeast culture.
   Cultivations of the fermentors were carried out at 30° C. at 150 rpm, without pH control for 92.5 hours.
   7-ml samples were taken twice the day by cut off pipette to monitor fermentation progress (ethanol concentration). The samples were transferred in 15 mL tubes and centrifuged at 4470 g for 10 minutes at 4° C. and stored until further analysis at −20° C.

B) Enzyme Product Activity Determination:
   DNSA solution: For the DNSA solution the following compounds were used:
   5.00 g 3,5-Dinitrosalicylic acid (DNSA) was dissolved in 300 ml distilled $H_2O$.
   add 50 ml NaOH/KOH-solution (4M KOH+4 M NaOH) drop per drop add 150 g K—Na-tartrate tetrahydrate
cool solution to room temperature
ad with destilled H$_2$O to 500 ml final volume
store in the darkness a) Pectinase
Substrates:
Polygalacturonic acid (Sigma 81325)
Substrates were dissolved in buffer to a concentration of 0.8% (w/v)
Buffer:
50 mM sodium acetate, pH 4.5

For the assay 96 well PCR microtiter plates (company Greiner) were used. The enzymes were diluted in buffer. 90 µl substrate and 10 µl enzyme solution were mixed. A blank was measured replacing enzyme solution with water. Incubation was carried out for 30 min at 37° C., followed by a 5 minute enzyme inactivation step at 99° C. and followed by cooling for 10 min at 4° C. In a second 96 well PCR microtiter plates (company Greiner) 50 µl of the incubated substrate—enzyme mix was incubated with 50 µl of the DNSA solution at 98° C. for 10 minutes and then cooled to 4° C. and incubated for 5 minutes at 4° C.

100 µl of the reaction was transferred into a well of 96 well transparent, flat bottom micro titer plate and the adsorption was measured at 540 nm by a micro titer plate reader (Tecan M1000).

b) Xylanase
Substrates:
Xylan from birchwood (Sigma X0502)
Substrate was dissolved in buffer to a concentration of 1.5% (w/v)
Buffer:
100 mM sodium acetate, pH 5.0 containing 20 mM CaCl$_2$ and 0.4 g/L Tween20

For the assay 96 well PCR microtiter plate (company Greiner) were used. The enzymes were diluted in buffer. 90 µl substrate and 10 µl enzyme solution were mixed. A blank was measured replacing enzyme solution with water. Incubation was carried out for 20 min at 40° C., followed by a 5 minute enzyme inactivation step at 99° C. and followed by cooling for 5 min at 4° C. 45.5 µL of the DNSA solution was added to the 96 well PCR microtiter plate by a multidrop (company Fisher-Scientific) and then the plate was incubated for 98° C. for 10 minutes and cooled to 4° C. and incubated for 5 minutes at 4° C.

100 µl of the reaction was transferred into well of a new 96 well transparent, flat bottom micro titer plate and then the adsorption was measured at 540 nm by a micro titer plate reader (Tecan M1000).

The activity is calculated as Units per µl or mg of enzyme product. 1 unit is defined as the amount of formed reducing ends µmol per minute. The enzyme activities are shown in Table 1.

TABLE 1

| Type | Activity | Shortname |
|---|---|---|
| pectinase | 90349 U/mL | Pec3 |
| xylanase | 10027 U/mL | Xyl16 |

Analysis of Ethanol

Frozen samples of the fermentation process were thawed up and the ethanol concentrations in the fermentation samples were measured by HPLC. Fermentation samples were centrifuged at 20000 g at 10° C. for 15 minutes and the supernatant was transferred into HPLC vials. The samples (30 µL) were injected into a VWR/Hitachi equipment comprising the isocratic pump L-2130, the auto-sampler L-2200, the column oven L-2350, the refractic index detector L-2490 and a degasser at 10° C. The EZ Chrome Elite 3.3.1 software was used. The VWR/Hitachi HPLC was equipped with a Rezex ROA Organic Acid H+(8%) LC column (300×7.8 mm, Phenomenex, Torance Calif.) and a guard column (carbo-H 4×3.0 mm, Phenomenex, Torance Calif.). The column was eluted with 0.0025 M H$_2$SO$_4$ at 0.45 mL/min flow rate at 60° C. The system was standardized by a 6-point calibration ethanol standard (100 g/L, 50 g/L, 25 g/L, 12.5 g/L, 6,125 g/L and 0 g/L ethanol).

TABLE 2

| | ethanol [g/L] | | |
|---|---|---|---|
| Growth time [h] | 0 g/t pectinase plus 0 g/t xylanase | 75 g/t pectinase plus 75 g/t xylanase | 200 g/t pectinase plus 200 g/t xylanase |
| 1 | 0.0 | 0.0 | 0.0 |
| 21.5 | 39.3 | 41.0 | 41.0 |
| 29.75 | 51.3 | 53.7 | 54.5 |
| 46.5 | 69.4 | 74.9 | 75.4 |
| 54 | 76.8 | 81.8 | 80.0 |
| 69 | 80.8 | 81.6 | 81.8 |
| 76 | 81.3 | 82.4 | 82.1 |
| 92.5 | 81.8 | 81.8 | 82.9 |

Figure 2:
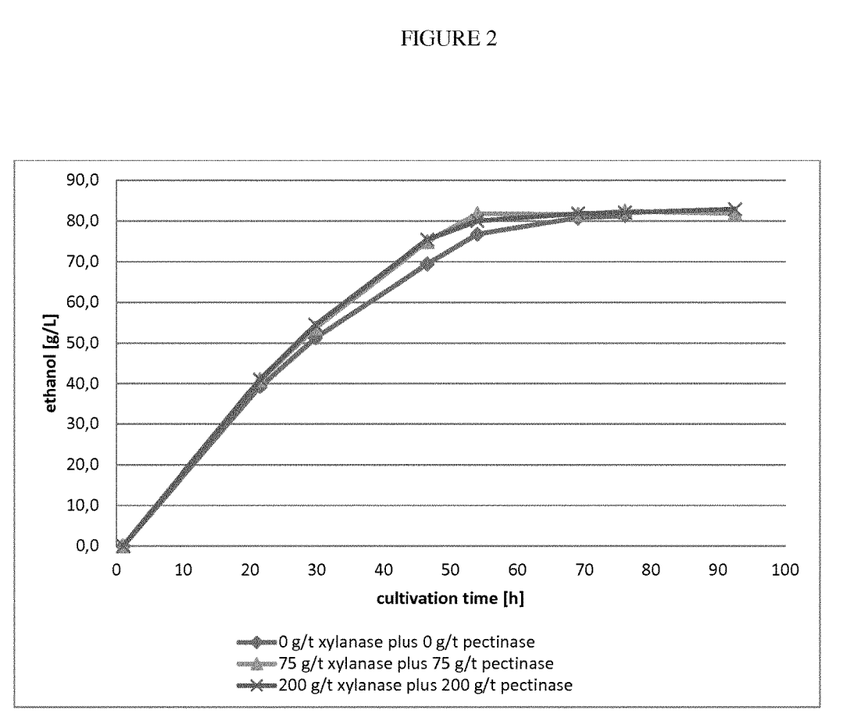
FIG. 2 is a diagram showing the time course of production of ethanol during the fermentation process in presence (75 g/t and 200 g/t) and absence (0 g/t) of the enzyme composition comprising a xylanase plus a pectinase.
Figure 3:
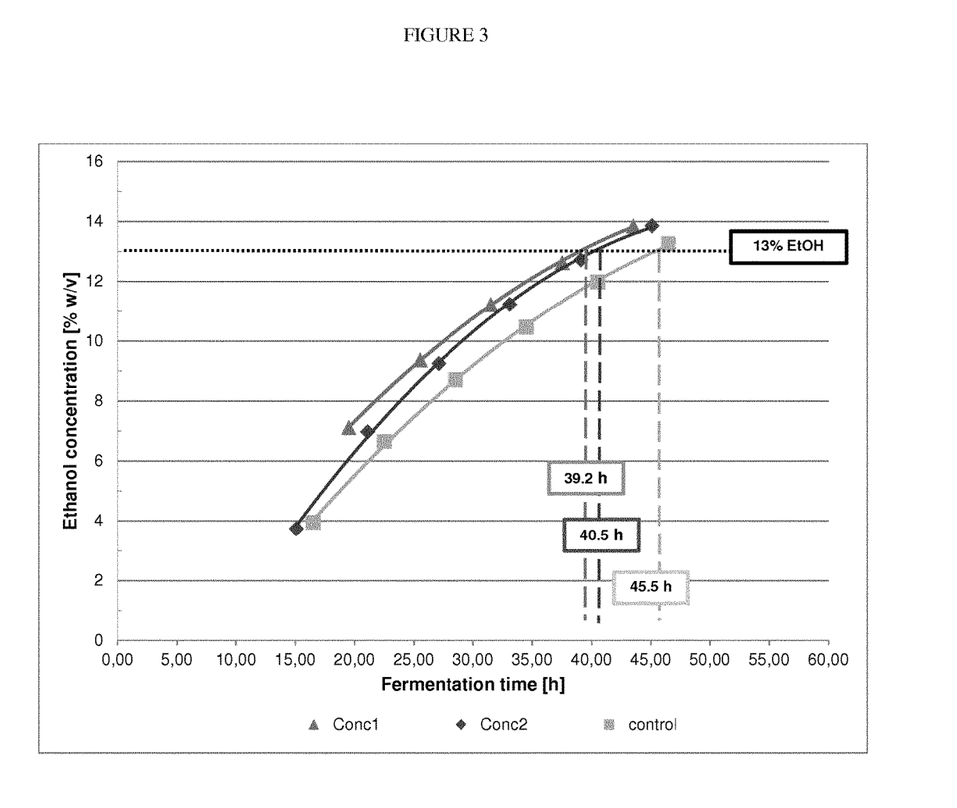
FIG. 3 is a diagram showing the effect of an enzyme composition comprising at least a xylanase and a pectinase on ethanol fermentation performance. Determination of the ethanol production is shown exemplarily for selected fermentation batches for Control, Conc1 and Conc2.

FIG. 2: Time course of production of ethanol during the fermentation process in presence (75 g/t and 200 g/t) and absence (0 g/t) of the enzyme composition comprising a xylanase plus a pectinase.

Table 2 and FIG. 2 shown that a treatment with the enzyme composition comprising a xylanase and a pectinase (75 g/t and 200 g/t of both enzymes) accelerates the production of ethanol during the fermentation process compared to the absence of enzyme composition comprising a xylanase and a pectinase (0 g/t of both enzymes).

What is claimed is:

1. A method of reducing a batch time in a fermentation process, the method comprising the steps of:
   i) converting starch containing material to fermentable sugars, wherein the starch containing material is corn;
   ii) fermenting the fermentable sugars with a microorganism into fermented mash;
   iii) subjecting fermentation medium during the fermentation process to an enzyme composition consisting of a xylanase and a pectinase; and
   iv) separating fermentation product from the fermented mash, wherein the fermentation product is ethanol.

2. The method according to claim 1, wherein the microorganism is selected from the group consisting of a bacteria, a yeast, and a fungi.

* * * * *